United States Patent
Hushek et al.

[11] Patent Number: 5,810,729
[45] Date of Patent: Sep. 22, 1998

[54] METHOD FOR MEASURING AND ADDING LIMB ANGLE INDICIA TO MR IMAGES

[75] Inventors: Stephen G. Hushek, Brookfield; Michael R. Figueira, Waukesha; Elizabeth A. Kuhn, Wauwatosa; Carl S. Winalski, Westwood, all of Wis.

[73] Assignee: General Electric Company Medical Systems, Waukesha, Wis.

[21] Appl. No.: 723

[22] Filed: Dec. 30, 1997

[51] Int. Cl.⁶ ........................................... A61B 5/05
[52] U.S. Cl. ..................... 600/410; 324/307; 324/309
[58] Field of Search ................... 600/410, 411, 600/415, 422; 324/307, 309

[56] References Cited

U.S. PATENT DOCUMENTS

| | | | |
|---|---|---|---|
| 4,803,431 | 2/1989 | Sano et al. ........................... | 324/306 |
| 5,329,924 | 7/1994 | Bonutti ................................. | 128/653.1 |
| 5,349,956 | 9/1994 | Bonutti ................................. | 128/653.1 |
| 5,403,350 | 4/1995 | Battocletti et al. ..................... | 324/306 |
| 5,562,092 | 10/1996 | Bonutti ................................. | 128/653.1 |
| 5,577,503 | 11/1996 | Bonutti ................................. | 128/653.2 |
| 5,640,958 | 6/1997 | Bonutti ................................. | 128/653.2 |
| 5,724,970 | 3/1998 | Vortruba et al. ...................... | 128/653.2 |
| 5,743,264 | 4/1998 | Bonutti ................................. | 128/653.2 |

*Primary Examiner*—Marvin M. Lateef
*Assistant Examiner*—Eleni Mantis Mercader
*Attorney, Agent, or Firm*—Quarles & Brady

[57] ABSTRACT

MRI images are acquired as the patient moves a joint through a range of motion. The angle of joined limbs is measured during the scan, and the measured angles are attached to corresponding images for display therewith. In one embodiment the angles are measured using interleaved navigator acquisitions from which limb orientation can be determined.

10 Claims, 3 Drawing Sheets

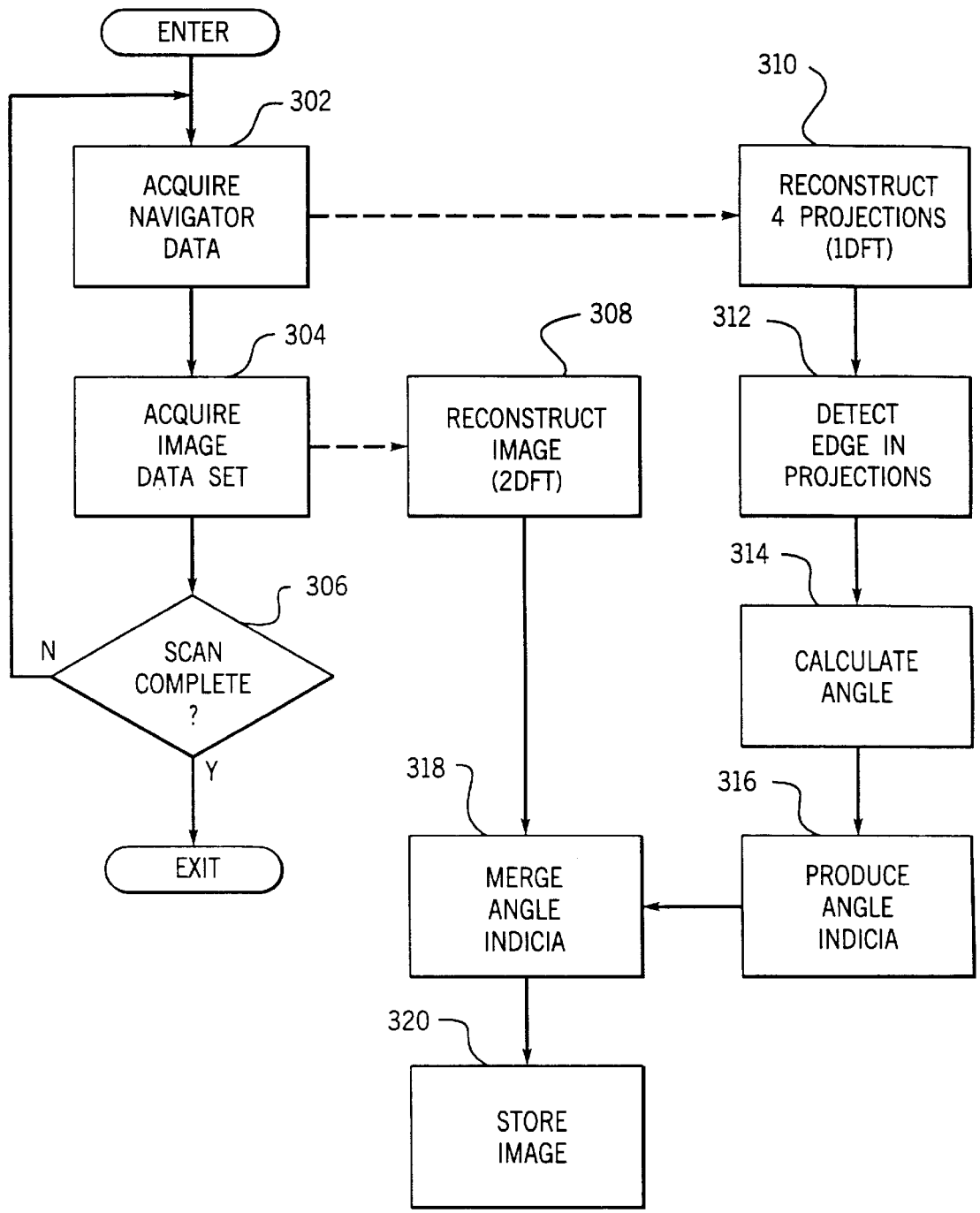

METHOD FOR MEASURING AND ADDING LIMB ANGLE INDICIA TO MR IMAGES

BACKGROUND OF THE INVENTION

The field of the invention is nuclear magnetic resonance imaging methods and systems. More particularly, the invention relates to the imaging of joints at a series of limb angles.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_1$. A signal is emitted by the excited spins after the excitation signal $B_1$, is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

One medical application of MRI is to image the structures of a joint as the patient moves the associated limbs through a range of motion. For example, a series of images might be acquired of the human knee joint as the patient moves through the entire range of knee motion. The resulting series of images depict the knee joint at a succession of limb angles, but the limb angle may not be apparent from the image. For example, a series of axial images through the knee to watch the movement of the patella would not reveal the angle defined by the femur and tibia. On the other hand, a series of sagittal images through the knee would reveal the orientation of the femur and tibia and enable the orthopedic surgeon to manually measure the angle on each image. Even when the angle is revealed by the image, the manual measurement is very time consuming, particularly when a large number of images are acquired.

SUMMARY OF THE INVENTION

The present invention is a method for measuring limb angle during an MRI scan and attaching to the reconstructed image indicia indicative of the measured angle. More particularly, a series of MR images are acquired during a scan in which the patient moves through a range of motion; data is acquired during the scan which indicates the relative location of two patient limbs as each MR image is acquired; each MR image is reconstructed and the corresponding location data is employed to calculate a limb angle; and the calculated limb angle is employed to produce angle indicia on the corresponding reconstructed image.

A general object of the invention is to automatically measure limb angle during an MRI scan and automatically attach the measured angle to the reconstructed image. No manual operations are performed. The location data is acquired automatically as the scan is performed and the MRI system calculates the angle at which each image is acquired and imprints the angle on the reconstructed image.

Yet another aspect of the invention is to measure limb angle without the addition of any hardware. Projection images are acquired in an interleaved manner during the scan to detect the orientation of limbs. From this acquired orientation data, the angle between the limbs is calculated. The projection images are acquired with the same MRI system used to acquire the images, and no additional hardware is required.

BRIEF DESCRIPTION OF THE DRAWINGS

FIG. 4 is a flow chart of a scan performed according to the preferred embodiment of the invention.

DESCRIPTION OF THE PREFERRED EMBODIMENT

Figure 1:
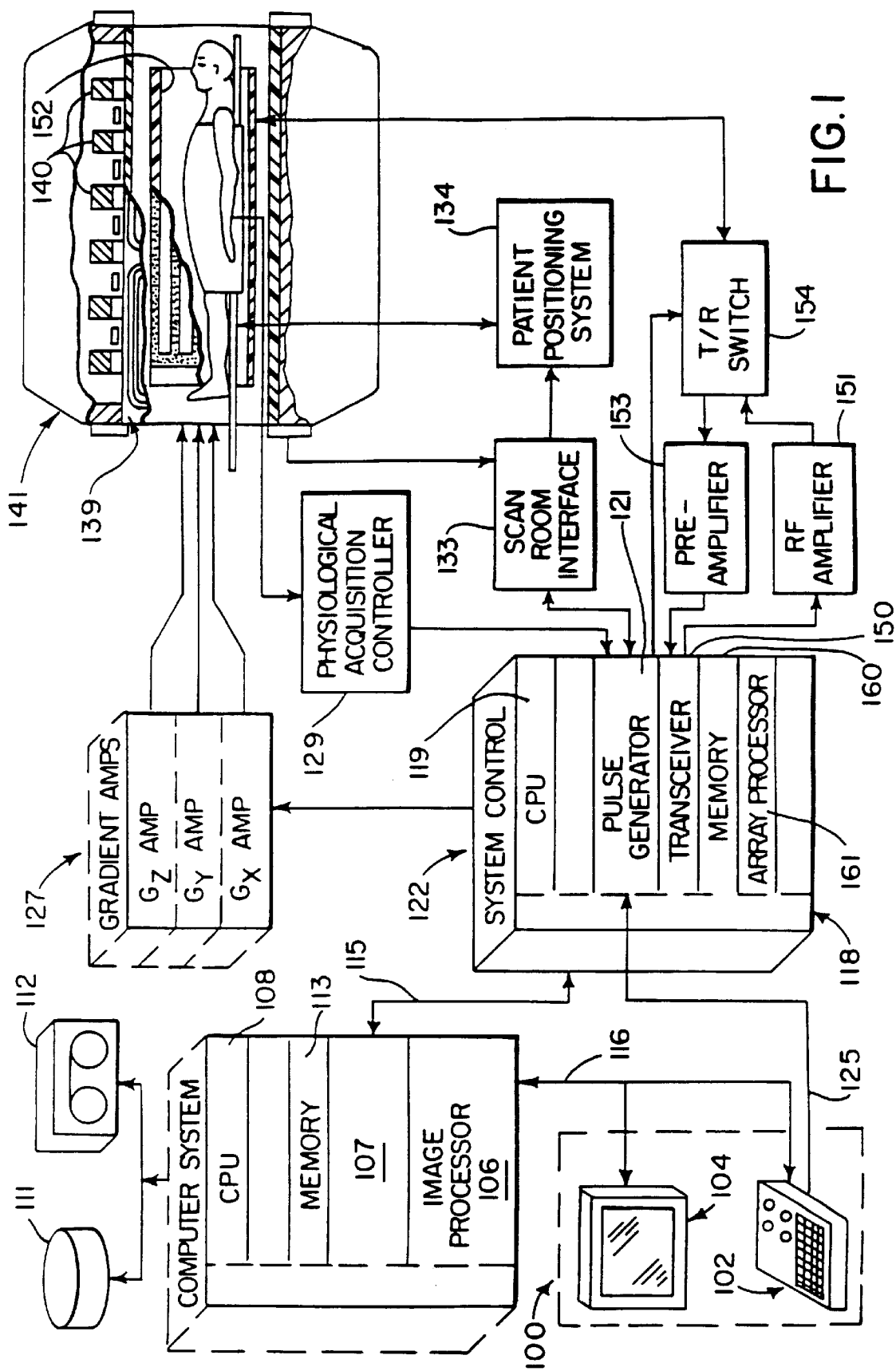
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

Figure 2:
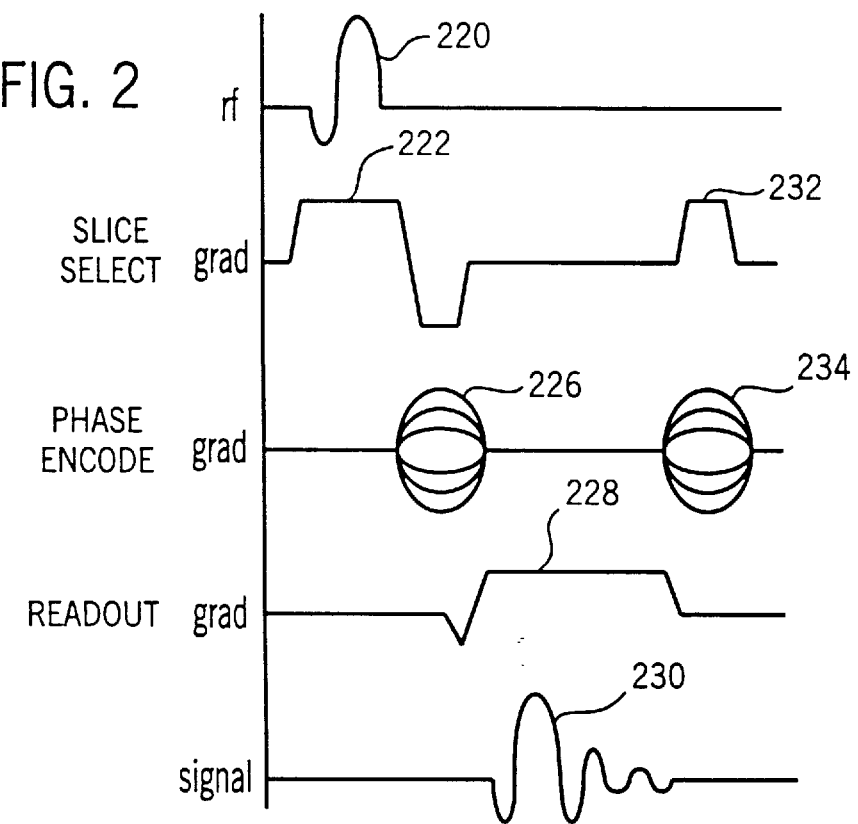
FIG. 2 is a graphic presentation of a pulse sequence employed to acquire the image data and the projection data according to the preferred embodiment of the invention.

While many pulse sequences may be used to practice the present invention, in the preferred embodiment a 2D gradient-recalled echo pulse sequence is used to acquire the NMR data. Referring particularly to FIG. 2, an RF excitation pulse 220 having a flip angle of 50° is produced in the presence of a slice select gradient pulse 222 to produce transverse magnetization in the 2D slice of interest. This is followed by a phase encoding gradient pulse 226 directed along the y axis. A readout gradient pulse 228 directed along the x axis follows and a partial echo (60%) NMR signal 230 is acquired and digitized as described above. After the acquisition, a spoiler gradient pulse 232 is applied along the z axis and a rewinder gradient pulse 234 is applied to rephase the magnetization before the pulse sequence is repeated as taught in U.S. Pat. No. 4,665,365.

As is well known in the art, the pulse sequence is repeated and the phase encoding pulse 226 is stepped through a series of values to sample the 2D k-space in the field of view. In the preferred embodiment 256 phase encodings are employed along the y axis. Sampling along the $k_x$ axis is performed by sampling the echo signal 230 in the presence of the readout gradient pulse 228 during each pulse sequence. It will be understood by those skilled in the art that only a partial sampling along the $k_x$ axis is performed and the missing data is computed using a homodyne reconstruction or by zero filling. This enables the echo time (TE) of the pulse sequence to be shortened to less than 1.8 to 2.0 ms and the pulse repetition rate (TR) to be shortened to less than 10.0 msecs.

The present invention is employed when a series of images are acquired as the patient moves a body part through a range of motion. Typically, the subject matter is a joint and the images are acquired to determine how the structures in the joint function throughout its range of motion. When examining the resulting images, an important diagnostic consideration is the orientation, or angle of the joint depicted by each image. In the preferred embodiment described below the invention is applied to the human knee, however, it can be appreciated by those skilled in the art that it is equally applicable to other locations in the body where it is important to know the angle of associated structures as the images are being acquired.

Figure 3:
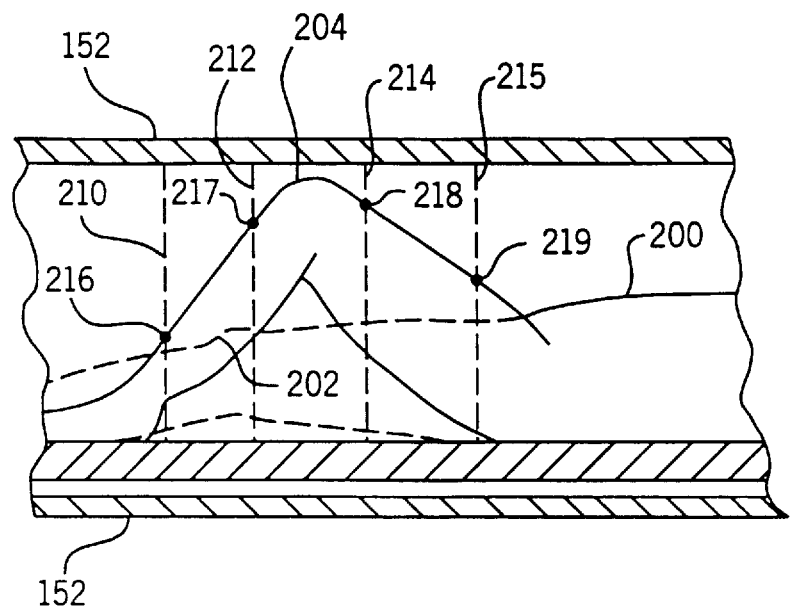
FIG. 3 is a pictorial representation of the acquisition of projection data using the pulse sequence of FIG. 2.

Referring particularly to FIG. 3, the patient 200 is positioned in the bore of the magnet with his knee located near the isocenter of the system. As a series of images are acquired, the patient is instructed to slowly move the knee joint from a straight orientation indicated by dashed lines 202 to a bent orientation indicated at 204. Navigator data is acquired in an interleaved manner during the scan and this navigator data is employed to measure the angle at the knee joint by measuring the orientation of the upper leg segment and the orientation of the lower leg segment.

Referring particularly to FIGS. 2 and 3, the pulse sequence used to acquire the navigator data is substantially the same as that described above and used to acquire the image data. However, no phase encoding pulses 226 and 234 are employed so that the signals are summed together to form a projection image. The slice select gradient is applied along the z-axis and the transmit frequency is set in each of four separate navigator signal acquisitions to select two axial slices through the lower leg segment as indicated by lines 210 and 212 and two axial slices through the upper leg segment as indicated by lines 214 and 215. The projections are positioned such that two of them intersect the upper edge of the lower leg throughout the range of motion and two of them intersect the upper edge of the upper leg segment. It may be necessary to orient the slices at an oblique angle, or move the location of the navigator projections during the scan to accomplish this.

Referring particularly to FIG. 4, the scan is performed by interleaving the acquisition of the navigator data as indicated at process block 302 with the acquisition of the image data as indicated at process block 304. Four navigator acquisitions are acquired as described above, and then an entire image frame is acquired using the prescribed imaging pulse sequence. The process repeats to acquire a series of image frames and associated navigator data until the scan is completed as determined at decision block 306. For example, 60 image frames might be acquired of the knee during a scan lasting two minutes (2 secs./image).

Referring still to FIG. 4, each acquired image data set is reconstructed into an image as described above and indicated at process block 308. For most scans this is a two-dimensional Fourier transformation, although three-dimensional images may also be produced. Each of the associated navigator signals are processed at 310 to produce four projections. This is a one-dimensional Fourier transformation along the readout gradient axis and it yields 256 intensity values which depict the total signal strength projected perpendicular to the readout gradient axis. The intensity values in each projection are examined at process block 312 to locate where, along the readout gradient axis, the signal strength steps up in value to indicate the top edge of the patient's leg. An edge detector such as that described by John F. Canny, "Finding Edges and Lines in Images", MIT Artificial Intelligence Laboratory, Technical Report No. 702, 1983, may be used for this purpose, and the upper rather than the lower edge is selected. As shown in FIG. 3, the four edge locations indicated at 216–219 are produced.

Using the four detected edge locations 216–219, the angle of the knee joint is calculated at process block 314. The slope of the line defined by the two edge points 218 and 219 on the upper leg segment is calculated, as is the slope of the line defined by the two edge points 216 and 217 on the lower leg segment. The knee joint angle (θ) is then calculated from these slopes ($m_1$ and $m_2$):

$$\bar{v}_1 = \begin{bmatrix} 1 \\ m_1 \end{bmatrix} \frac{1}{\sqrt{1+m_1^2}}$$

$$\bar{v}_2 = \begin{bmatrix} 1 \\ m_2 \end{bmatrix} \frac{1}{\sqrt{1+m_2^2}}$$

$$\theta = \cos^{-1}(\bar{v}_1 \cdot \bar{v}_2)$$

where $\bar{v}_1$, is the unit vector from edge point 218 to 219, and $\bar{v}_2$ is the unit vector from edge point 216 to 217.

The calculated angle (θ) may be displayed in a number of ways. It may be displayed simply as a number, as a pictorial icon, or both. Regardless of the format used, an angle indicia is produced at process block 316. This angle indicia is a two-dimensional array of pixel intensity values which are merged at process block 318 with the reconstructed image of the knee. The angle indicia replaces the pixel values at a location in the image selected by the operator. The finished image is stored at process block 320 and may be recalled for viewing on the display 104.

It should be apparent to those skilled in the art that many variations are possible from the preferred embodiment described above. As an alternative to navigation projections, location apparatus may be attached to the patient to track limb motion during the scan and provide angle information for attachment to the acquired images. Such apparatus are disclosed for example, in U.S. Pat. Nos. 5,671,739; 5,577,502; 5,445,150; 5,437,277; 5,377,678; 5,353,795; 5,307,808; 5,271,400; 5,622,170 and 5,617,857, which are incorporated herein by reference. While limb angle is used to measure joint orientation other anatomic structures can also be tracked.

We claim:

1. A method for acquiring a series of MR images during a scan in which an anatomic structure being imaged is moved through a range of motion, the steps comprising:

a) acquiring a series of images with an MRI system using an NMR imaging pulse sequence;

b) measuring an angle at the anatomic structure for each acquired image;

c) reconstructing each acquired image to depict the anatomic feature at a series of angles; and d) attaching each measured angle to its corresponding reconstructed image to indicate the angle when the image is displayed.

2. The method as recited in claim 1 in which the measured angle is attached to the reconstructed image by replacing pixels in the reconstructed image with angle indicia.

3. The method as recited in claim 2 in which the angle indicia includes numeric characters that indicate the measured angle.

4. The method as recited in claim 1 in which the angle at the anatomic feature is measured in step b) using NMR navigator pulse sequences.

5. The method as recited in claim 4 in which the navigator pulse sequences are substantially the same as the NMR imaging pulse sequences except a phase encoding gradient pulse is not employed.

6. The method as recited in claim 4 in which the navigator pulse sequences acquire NMR data from which a set of projection images are reconstructed.

7. The method as recited in claim 6 in which the anatomic feature is a joint and the projection images intersect limbs connected by the joint.

8. The method as recited in claim 7 in which the orientation of each limb is calculated by detecting the edge of the limb in a projection image.

9. The method as recited in claim 8 in which the angle at the joint is calculated from the limb orientations.

10. The method as recited in claim 1 in which the angle at the anatomic feature is measured in step b) using an apparatus that moves with the anatomic structure.

\* \* \* \* \*